(12) United States Patent
Weber et al.

(10) Patent No.: US 6,743,185 B2
(45) Date of Patent: Jun. 1, 2004

(54) HANDLE ASSEMBLY FOR SURGICAL INSTRUMENT AND METHOD OF MAKING THE ASSEMBLY

(75) Inventors: Jeffrey S. Weber, Miami, FL (US); Gustavo Aguirre, Pembroke Pines, FL (US); Larry Rose, Pembroke Pines, FL (US); Peter K. Kratsch, Sunrise, FL (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/960,317

(22) Filed: Sep. 24, 2001

(65) Prior Publication Data

US 2002/0038119 A1 Mar. 28, 2002

Related U.S. Application Data

(60) Provisional application No. 60/234,931, filed on Sep. 26, 2000.

(51) Int. Cl.$^7$ .............................................. A61B 10/00
(52) U.S. Cl. .................... 600/564; 600/562; 29/517; 29/469.5; 606/205
(58) Field of Search .............................. 600/564, 562; 606/1, 205, 208; 29/517, 469.5

(56) References Cited

U.S. PATENT DOCUMENTS

| | | | | |
|---|---|---|---|---|
| 5,325,866 A | * | 7/1994 | Krzyzanowski | 600/564 |
| 5,454,378 A | * | 10/1995 | Palmer et al. | 600/564 |
| 5,462,527 A | * | 10/1995 | Stevens-Wright et al. | 604/528 |
| 5,638,827 A | | 6/1997 | Palmer et al. | |
| 5,762,069 A | * | 6/1998 | Kelleher et al. | 600/564 |
| 5,766,184 A | * | 6/1998 | Matsuno et al. | 606/142 |
| 5,810,876 A | | 9/1998 | Kelleher | |
| 6,007,560 A | * | 12/1999 | Gottlieb et al. | 606/205 |
| 6,015,381 A | | 1/2000 | Ouchi | |
| 6,099,483 A | * | 8/2000 | Palmer et al. | 600/564 |
| 6,210,398 B1 | | 4/2001 | Ouchi | |
| 6,299,630 B1 | | 10/2001 | Yamamoto | |
| 6,331,165 B1 | * | 12/2001 | Turturro et al. | 451/41 |

FOREIGN PATENT DOCUMENTS

| | | |
|---|---|---|
| DE | 199 24 639 A1 | 12/1999 |
| DE | 199 48 387 A1 | 5/2000 |

* cited by examiner

*Primary Examiner*—Max F. Hindenberg
*Assistant Examiner*—Jonathan Foreman
(74) *Attorney, Agent, or Firm*—Finnegan, Henderson, Farabow, Garrett & Dunner, LLP (57) ABSTRACT

A surgical instrument includes a handle assembly, a flexible conduit, and at least one control member axially movable in the flexible conduit. The handle assembly includes a body member configured to be coupled to the flexible conduit. An actuator is movable on the body member. The actuator includes at least one projection member. The assembly further includes a reinforcement tube having an interior passage sized to accommodate the control member. The reinforcement tube includes a least one bend configured to engage the at least one projection member such that movement of the actuator with respect to the body member causes movement of the reinforcement tube. Methods of manufacturing the handle assembly are also disclosed.

34 Claims, 8 Drawing Sheets

HANDLE ASSEMBLY FOR SURGICAL INSTRUMENT AND METHOD OF MAKING THE ASSEMBLY

The present application relies on the benefit of priority of U.S. provisional patent application No. 60/234,931, filed on Sep. 26, 2000.

BACKGROUND OF THE INVENTION

1. Field of the Invention

The present invention relates generally to a handle assembly for a surgical instrument having at least one axially movable control member. More particularly, this invention relates to a proximal handle assembly for an endoscopic biopsy instrument.

2. Description of the Related Art

Endoscopic biopsy procedures are performed with an endoscope and an endoscopic biopsy instrument. An endoscopic biopsy instrument is a flexible medical device for insertion into a body passageway or cavity that enables a surgeon at a remote external location to remove and retrieve a tissue sample from a site internal to the patient's body. The biopsy instrument typically includes an elongated flexible member having a tissue sampler at the distal end and a handle assembly with a manual actuator at the proximal end.

During a biopsy tissue sampling operation, a surgeon guides the endoscope to the biopsy site within the body of the patient. The biopsy instrument is then inserted through the endoscope until the tissue sampler is proximate to the tissue to be sampled. The surgeon manipulates the actuator so that the tissue sampler tears or cuts away a sample of tissue from the biopsy site and retains the tissue sample.

Most endoscopic biopsy instruments have one or more control members, such as wires, extending through a flexible conduit typically having a wire coil. A distal end of each control member is typically connected to a tissue sampler or some other form of end effector located at a distal end of the flexible conduit. A proximal end of each control member is connected to the actuator of the proximal handle assembly such that movement of the actuator causes axial movement of the control members and thereby actuates the tissue sampler. For example, distal movement of the control members causes opening of jaws of the tissue sampler and proximal movement of the control members causes closing of the jaws, or vice versa.

There are a variety of drawbacks and disadvantages associated with some conventional handle assemblies for surgical instruments including endoscopic biopsy instruments. For example, some of these assemblies have a number of separate components that must be assembled together in relatively costly and or complex manufacturing processes. In one conventional handle design, the control members are attached to the actuator of the handle assembly via an anti-kinking member, set screw, and a cross pin which is configured to be placed in the actuator. The control members are passed through the anti-kinking member and the set screw is tightened in the cross pin to attach both the control members and the anti-kinking member to the combination of the cross pin and the actuator. Although such a configuration provides an effective attachment of the control members to the actuator, it could be less expensive if the number of parts was reduced.

Attachment of the handle assembly to the flexible conduit is another aspect of surgical instruments that could be improved. Various apparatuses have been used to attach the flexible conduit to the handle assembly. Considerations include cost, ease of component manufacture, ease of assembly, expected life cycle of the biopsy instrument, operational loads, and acceptance by the operator. Surgeons would find unacceptable any attachment apparatus that permits the flexible conduit to move relative to the handle during manipulation of the end effectors.

One method of attaching the coil to the handle is bonding. This may be acceptable for disposable biopsy instruments, but not for instruments that are to be autoclaved. Repeated autoclaving may degrade the bondline. Furthermore, bonding raises OSHA/SHEA concerns regarding the exposure of assembly workers to solvent fumes.

In another example, a barbed crimp band is crimped onto the end of the flexible conduit and press fitted into an inner bore of the handle. Such an assembly could be improved if it was less expensive. Additionally, press fitting the barbed crimp band into the handle may also result in unacceptably large tensile hoop stresses in the handle that may ultimately lead to cracks. Furthermore, this design might create an undesirably large gap between the outer diameter of the flexible conduit and the inner bore of the handle, leaving the flexible conduit unsupported within the handle and prone to bending displacements.

BRIEF SUMMARY

The present invention is directed to structural arrangements and methods that optionally obviate one or more of the limitations of the related art. As embodied and broadly described herein, one aspect of the invention includes a handle assembly for a surgical instrument having a flexible conduit and at least one control member axially movable with respect to the flexible conduit. The handle assembly includes a body member configured to be coupled to the flexible conduit. An actuator is movable on the body member. The actuator includes at least one projection member. The assembly further includes a reinforcement tube having an interior passage sized to accommodate the control member. The reinforcement tube includes at least one bend configured to engage the at least one projection member such that movement of the actuator with respect to the body member causes movement of the reinforcement tube.

As used herein, the term "surgical instrument" is not limited to instruments used in what are sometimes considered to be surgical procedures. In particular, the term "surgical instrument" relates to a variety of different forms of medical instruments used, for example, for a variety of differing bodily diagnoses and/or treatments.

In another aspect, the invention includes a handle assembly comprising a body member including portions configured to be connected together to retain the flexible conduit therebetween.

In yet another aspect, the invention includes a surgical instrument including the handle assembly, a flexible conduit coupled to the body member, and at least one control member axially movable in the flexible conduit. Preferably, at least one end effector is at a distal end of the flexible conduit. The end effector could be linked to the control member such that axial movement of the control member causes activation of the end effector.

In an even further aspect, the invention includes a method of making a handle assembly, the method includes placing at least one control member in a reinforcement tube, bending the reinforcement tube to form at least one bend in the reinforcement tube, the at least one bend reducing the interior cross-section of the tube and thereby retaining the control member in the reinforcement tube, and engaging the at least one bend with at least one projection member associated with an actuator movable on a body member such that movement of the actuator with respect to the body member causes movement of both the reinforcement tube and the control member.

In an additional aspect, the invention includes a method of connecting a handle assembly to a flexible conduit of a surgical instrument. The method includes providing a handle assembly including a body member and an actuator movable on the body member, wherein the body member includes portions configured to be connected together to retain the flexible conduit therebetween, placing the flexible conduit between the portions of the body member, and connecting the portions of the body member together to retain the flexible conduit therebetween.

It is to be understood that both the foregoing general description and the following detailed description are exemplary and explanatory only and are not restrictive of the invention.

BRIEF DESCRIPTION OF THE DRAWINGS

The accompanying drawings, which are incorporated in and constitute a part of this specification, illustrate several exemplary embodiments of the invention and together with the description, serve to explain at least some of the principles of the invention. In the drawings.

DESCRIPTION OF THE EXEMPLARY EMBODIMENTS

Reference will now be made in detail to exemplary embodiments of the invention, examples of which are illustrated in the accompanying drawings. Wherever possible, the same reference numbers will be used throughout the drawings to refer to the same or like parts.

The present invention generally relates to a handle assembly for a surgical instrument. For example, the instrument could be an endoscopic instrument, such as an endoscopic biopsy instrument. While the exemplary embodiment shown in the drawings is described herein in connection with a biopsy forceps device, it is understood that the invention may be used in connection with various other endoscopic and nonendoscopic surgical instruments.

Figure 1:
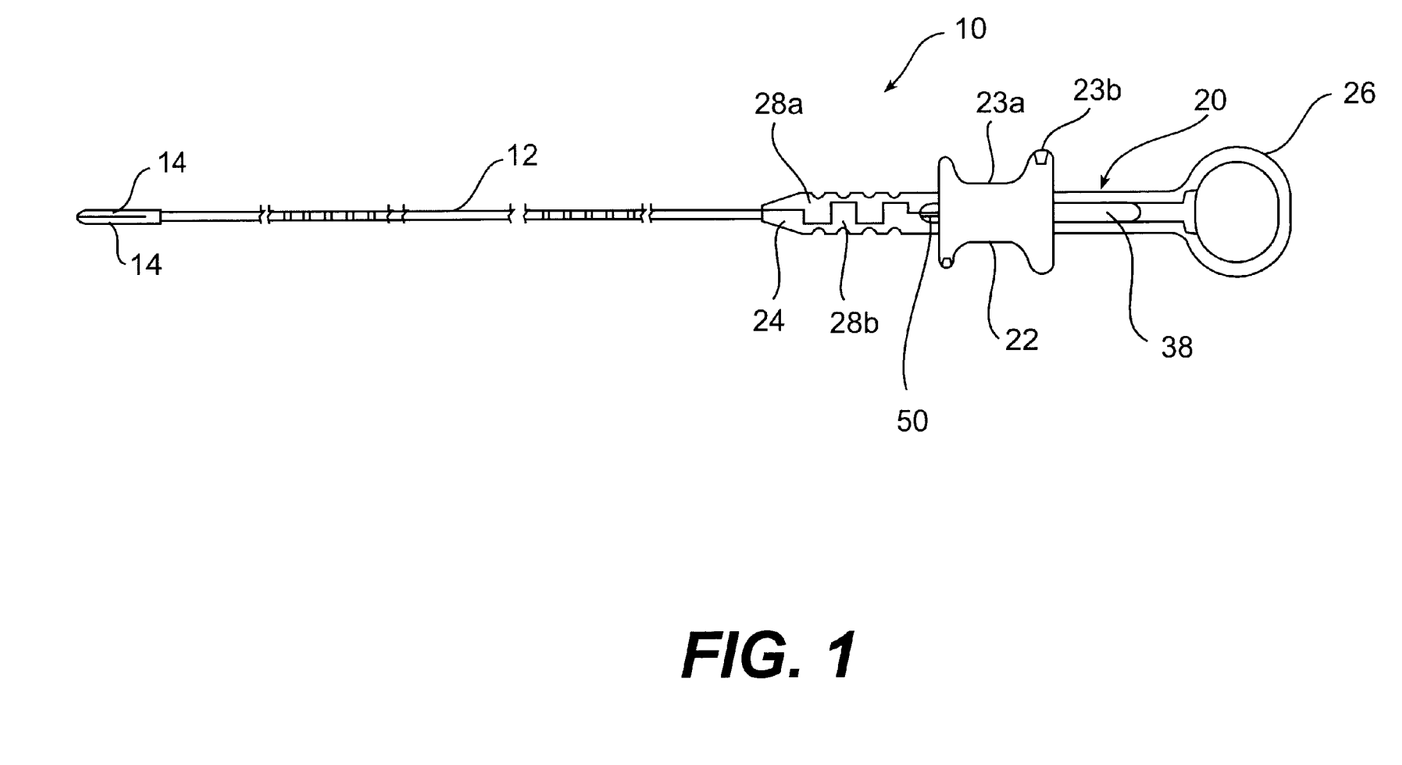
FIG. 1 is a side view of an exemplary embodiment of an endoscopic biopsy instrument including a handle assembly according to the present invention.

FIG. 1 shows an exemplary embodiment of an endoscopic biopsy instrument 10 including a flexible conduit 12, a handle assembly 20 connected to a proximal end of the conduit 12, and a pair of jaw-like end effectors 14 (e.g., biopsy forceps end effectors) provided at a distal end of the conduit 12. One or more control members 16 (FIG. 8) extend through the conduit 12 and have a proximal end coupled to a movable actuator 22 on the handle assembly 20 and a distal end coupled to the end effectors 14. For example, distal movement of the actuator 22 could cause movement of the control members 16 in the distal direction to thereby place the end effectors 14 in an open position wherein distal ends of the end effectors 14 are separated from one another; and proximal movement of the actuator 22 could cause movement of the control members 16 in the proximal direction to thereby place the end effectors 14 in a closed position wherein the distal ends of the end effectors 14 are moved toward one another to apply a closing force.

In addition to the embodiment of FIG. 1 wherein a pair of end effectors 14 are arranged in a jaw-like form, there are many other possible end effector arrangements. For example, in an alternative embodiment the end effector arrangement could be in the form of a snare, such as a wire loop lasso for shearing a polyp.

Figure 2:
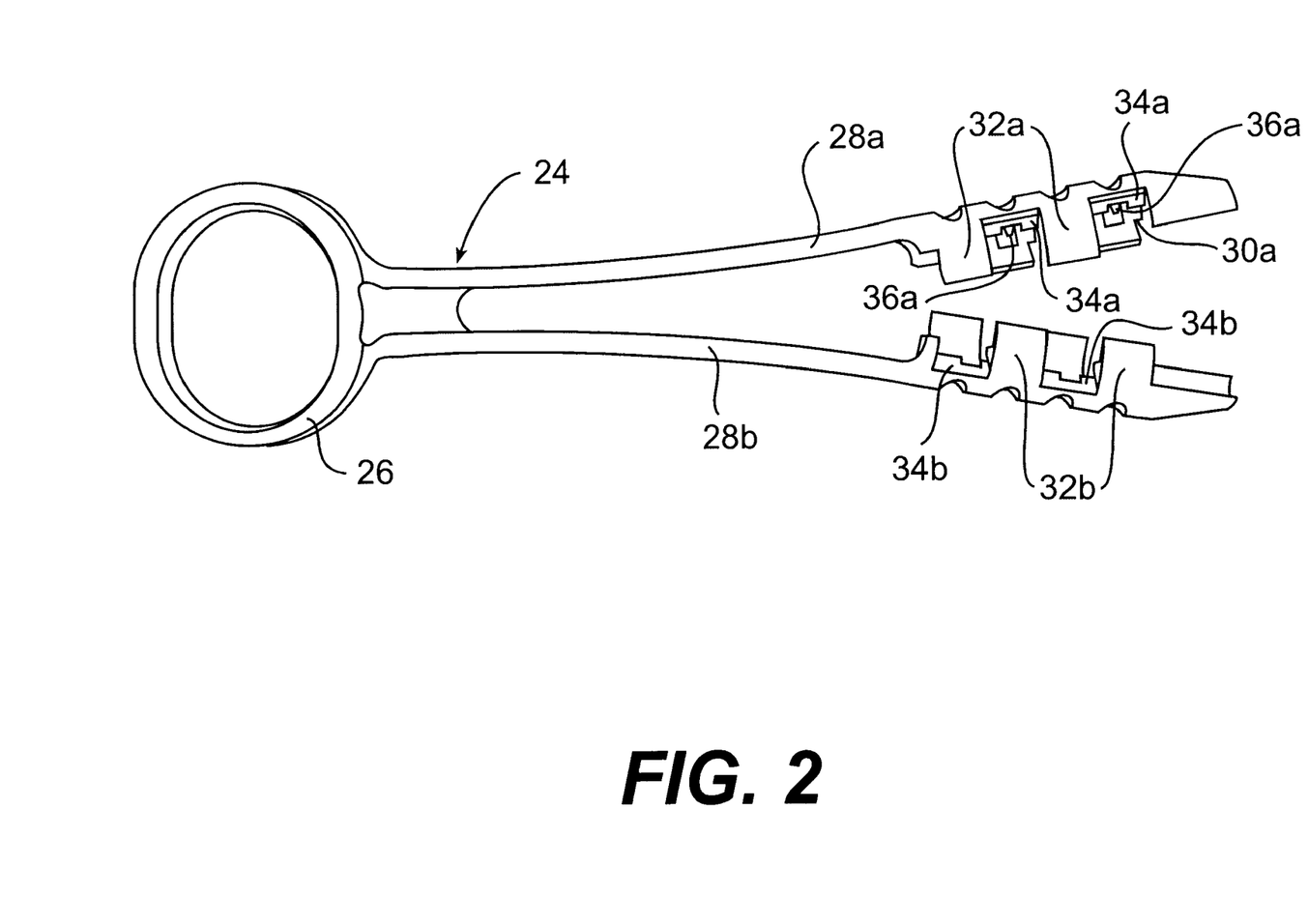
FIG. 2 is a perspective view of a body member of the handle assembly of FIG. 1 with the body member shown in its unassembled condition.
Figure 3:
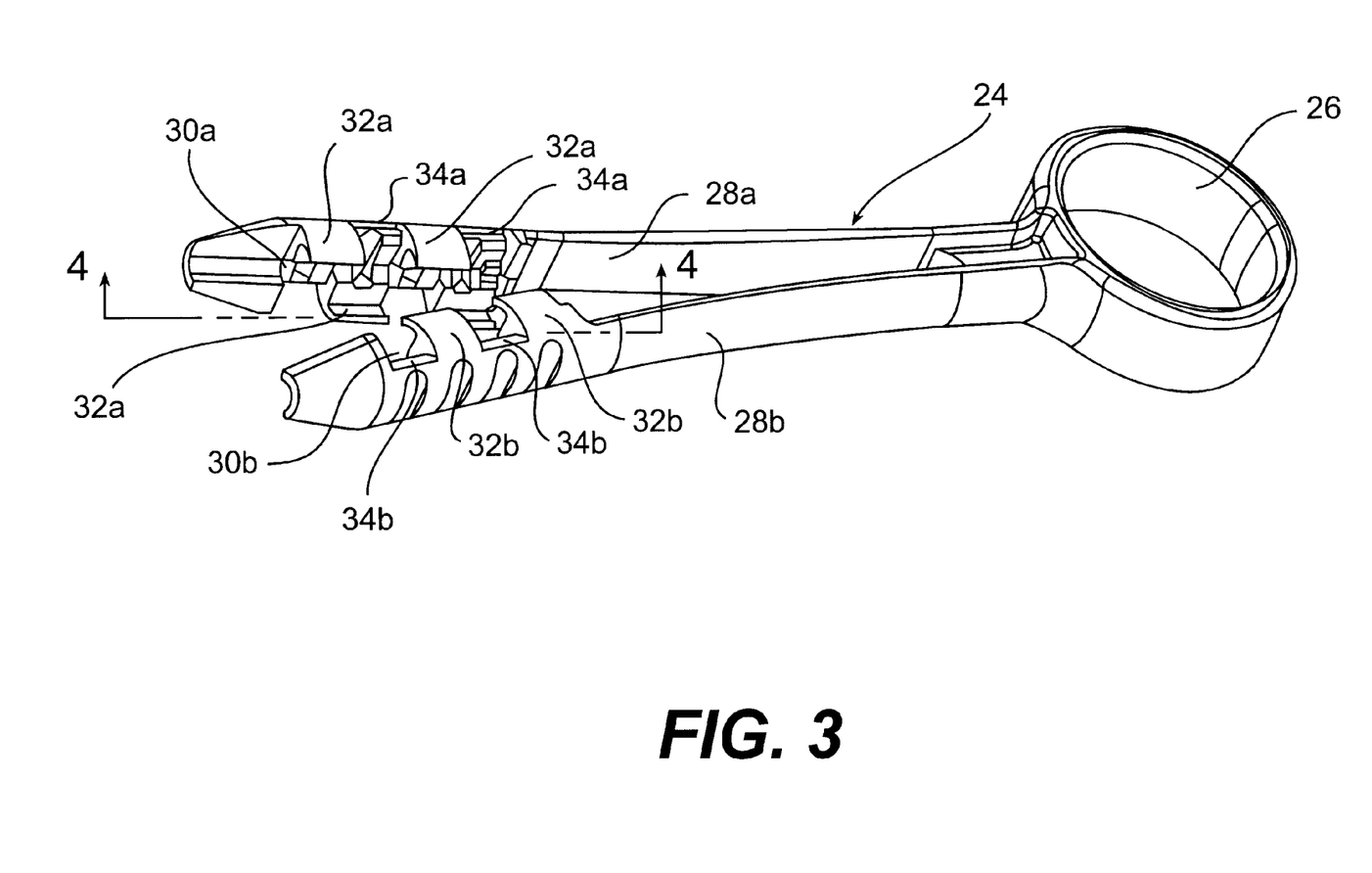
FIG. 3 is a view similar to that of FIG. 2 showing an opposite side of the body member.
Figure 5:
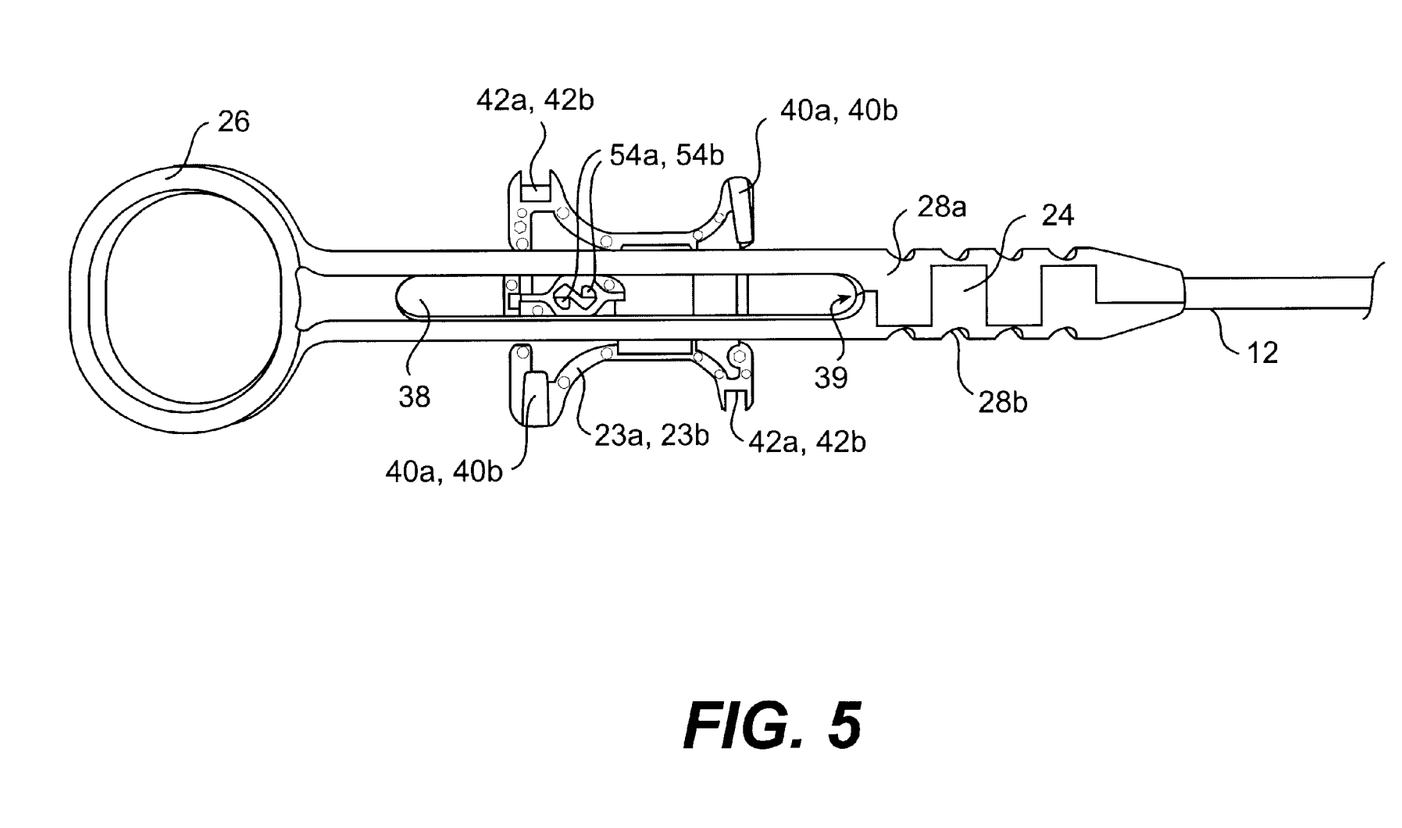
FIG. 5 is a side view showing portions of the handle assembly of FIG. 1 with the body member being in the assembled condition providing attachment to a flexible conduit and with one portion of an actuator positioned on the body member.
Figure 6:
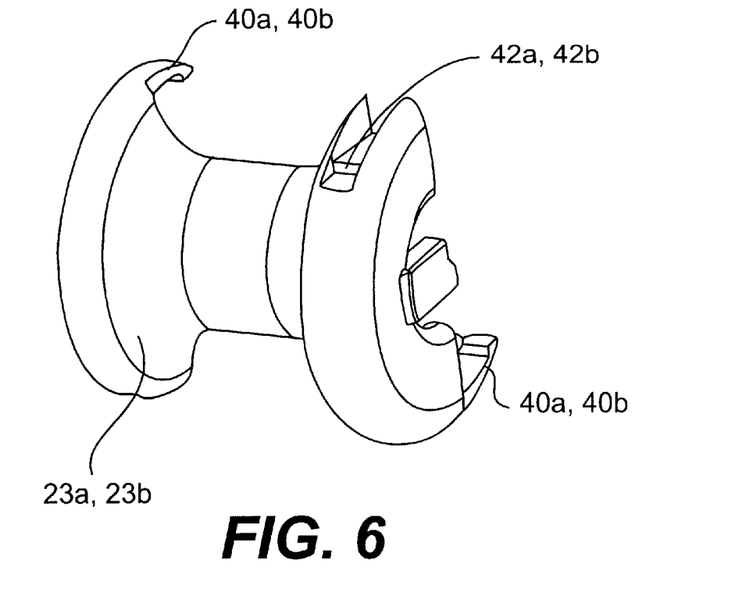
FIG. 6 is a outer side perspective view of one of the portions of the actuator of FIG. 1.
Figure 7:
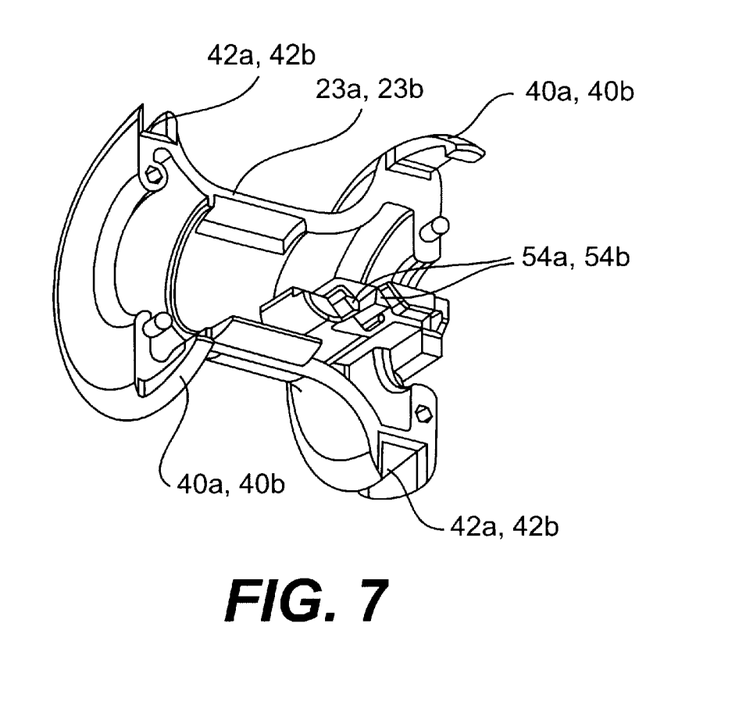
FIG. 7 is a inner side perspective view similar to FIG. 6 showing the inside of the actuator portion.

The handle assembly 20 includes a body member 24 on which the movable actuator 22 moves. FIGS. 2 and 3 show the body member 24 before it is connected to the remainder of the instrument. The body member 24 preferably includes a thumb ring 26 sized to accommodate the thumb of a user. Opposite arm portions 28a and 28b extend from the thumb ring 26. The distal end of each arm portion 28a, 28b includes a generally U-shaped channel 30a, 30b, clips 32a, 32b, and retainer ridges 34a, 34b. The body member 24 is preferably made of a flexible plastic permitting the arm portions 28a, 28b to be flexed toward one another so that the clips 32a, 32b become engaged with the corresponding ridges 34b, 34a, thus connecting the arm portions 28a, 28b together at their distal ends. The conduit 12 is placed between the arm portions 28a, 28b before they are connected, and the U-shaped channels 30a, 30b mate to form a bore for accommodating and gripping the conduit 12. Preferably, the inside diameter of this bore is at least slightly less than the outside diameter of the conduit 12. FIGS. 1 and 5 show the arm portions 28a and 28b connected together with the conduit 12 held therebetween.

Figure 4:
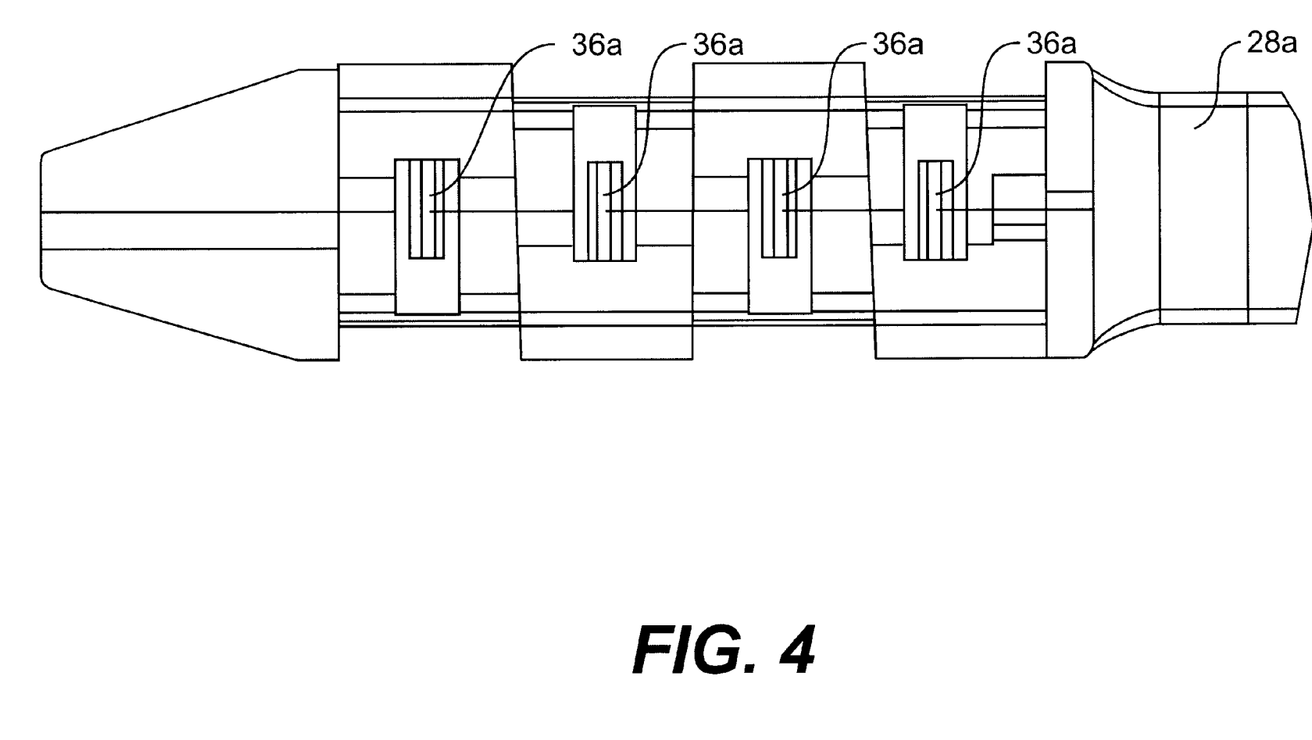
FIG. 4 is a view taken along line 4—4 of FIG. 3 showing an inner face of one of the two distal end portions of the body member.

As shown in FIGS. 2–4, the inner faces of both of the arm portions 28a, 28b include transverse ribs 36a, 36b configured to engage the outer surface of the conduit 12 and thereby lock the conduit 12 in the body member 24 when the arm portions 28a, 28b are connected. Optionally, the engagement of the clips 32a, 32b with the corresponding ridges 34b, 34a is a resilient snap connection that does not require any additional material, such as adhesive, or additional parts, such as retaining rings. Other connections between the arm portions 28a, 28b are, of course, possible.

When the arm portions 28a, 28b are connected together, a passageway 39 shown in FIG. 5 is formed in the body member 24, and a slot 38 is formed in the body member 24, as shown in FIGS. 1 and 5. An inner part of the actuator 22 travels in the slot 38.

In an exemplary embodiment, the actuator 22 is formed from two initially separate portions 23a, 23b (FIGS. 1 and 5–8), which are identical to one another. (For convenience, FIGS. 5–8 show one portion but have labels corresponding to either one of the portions 23a, 23b.) Each of the portions 23a, 23b includes clips 40a, 40b and ridges 42a, 42b. The clips 40a, 40b are configured to be engaged with corresponding ridges 42b, 42a to connect the portions 23a, 23b together with a snap connection. As with the body member 24, alternative connecting configurations are also possible.

The actuator portions 23a, 23b are connected together to form the actuator 22 while the body member 24 is positioned between them. This causes part of the actuator 22 to be in the slot 38 and another part of the actuator to extend around the body member 24. The actuator 22 is permitted to slide proximally and distally within the slot 38 and along the outside of the body member 24. The actuator 22 is generally shaped in the form of a spool having relatively enlarged disc ends.

Figure 8:
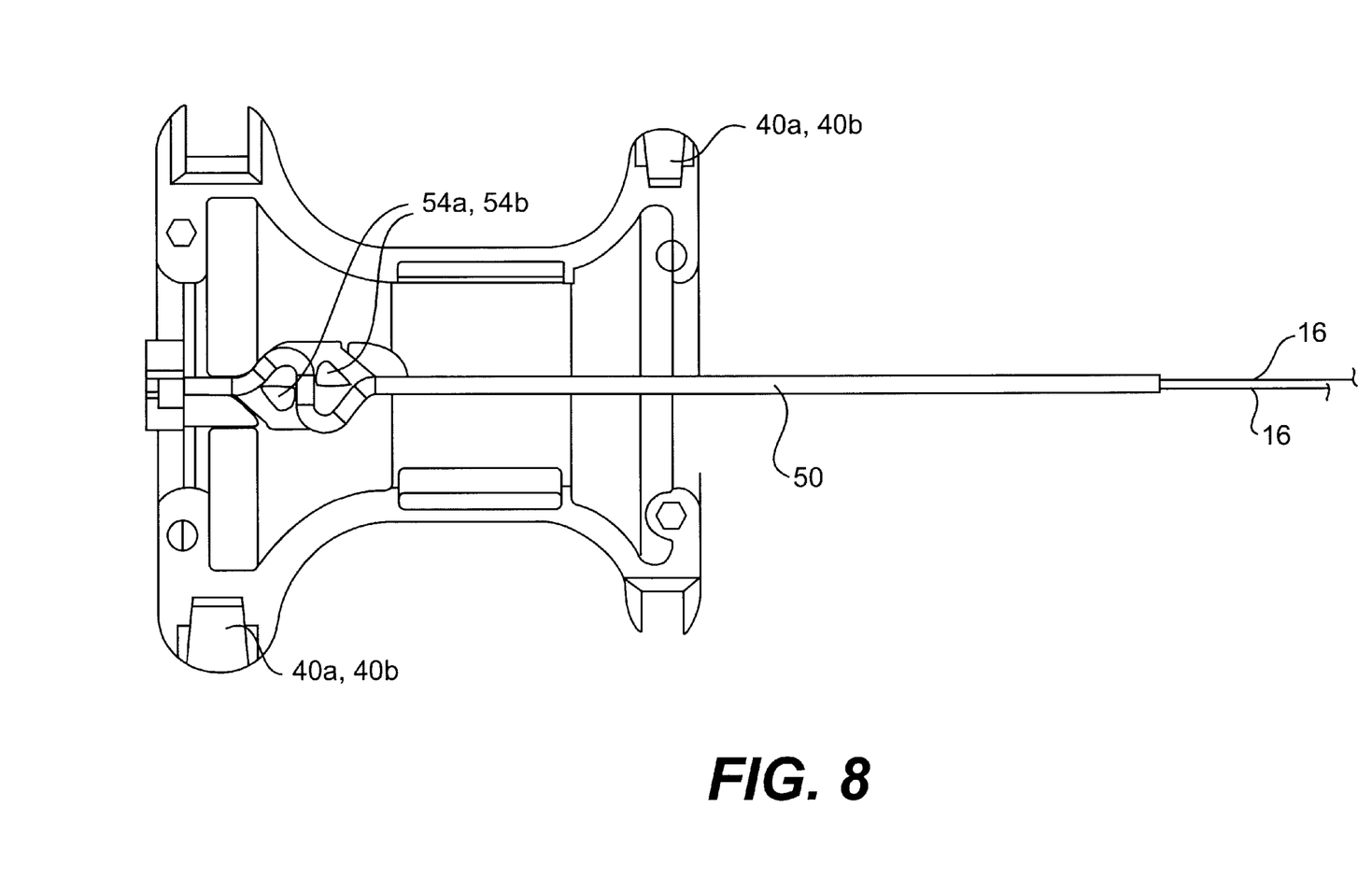
FIG. 8 is an inner side view of one of the portions of the actuator of FIG. 1 with a bent reinforcement tube positioned in the actuator portion and being attached to a pair of control members.
Figure 9:
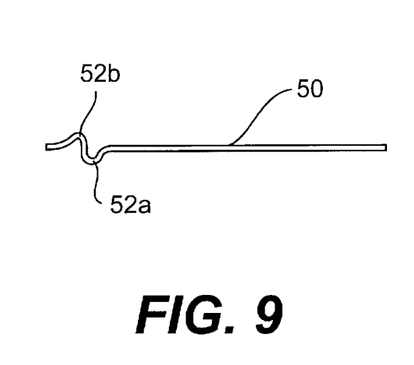
FIG. 9 is a side view of the bent reinforcement tube of FIG. 8.

As shown in FIGS. 1, 8, and 9, the handle assembly further includes a reinforcement tube 50 having one or more bends 52a, 52b formed in the tube's proximal end portion. Optionally, the tube 50 is formed of a relatively rigid material that is capable of being deformed by bending to form the bends 52a, 52b. An interior passage in the tube is sized to accommodate the control members 16. A proximal end of the control members 16 is retained in the reinforcement tube 50 via the reduced cross-sectional area of the reinforcement tube 50 in the region of the bends 52a, 52b. In one exemplary retaining method, the control members 16 are positioned in the tube 50 and placed under tension while the tube 50 is being bent by a forming pin that rotates. The bending causes the interior cross-section of the tube 50 to deform to a smaller size in the region of the bends 52a, 52b and thereby retains the control members 16 within the tube 50.

The bent reinforcement tube 50 is placed between the actuator portions 23a, 23b before the portions 23a, 23b are connected to one another. The tube 50 is positioned so that the bends 52a, 52b of the reinforcement tube 50 at least partially wrap around the projection members 54a, 54b on the interior of the actuator portions 23a, 23b to thereby engage the projection members 54a, 54b. Upon connecting the actuator portions 23a, 23b to one another, the projection member 54a, 54b form a tortuous path that generally corresponds and mates with the tortuous bend shape of the bends 52a, 52b in the reinforcement tube 50. This places the reinforcement tube 50 and the attached control members 16 in engagement with the actuator 22 such that proximal and distal movement of the actuator 22 with respect to the body member 24 causes corresponding proximal and distal movement of the reinforcement tube 50 and the control members 16. In the exemplary embodiment shown in the drawings, the columnar strength of the reinforcement tube 20 is sufficient to resist kinking of the proximal end portions of the control members during distal movement of the actuator 22, for example, when the control members 16 are movable wires.

During movement of the actuator 22, the reinforcement tube 50, and optionally also the control members, move in a slidable manner in the passageway 39 shown in FIG. 5. The passageway 39 leads to the conduit 12 engaged in the body member 24.

Figure 10:
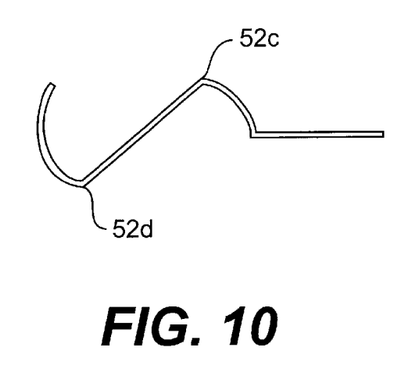
FIG. 10 is a side view of an end portion of a bent reinforcement tube according to a first alternative embodiment.
Figure 11:
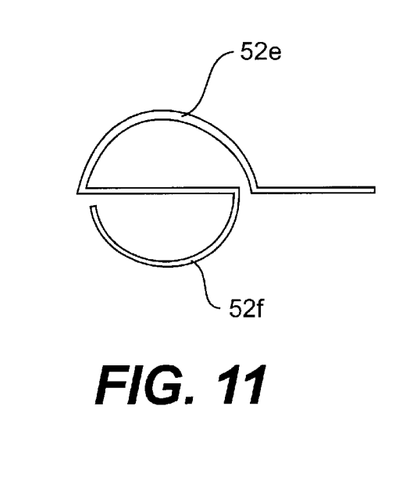
FIG. 11 is a view similar to FIG. 10 showing a second alternative embodiment of the bent reinforcement tube.
Figure 12:
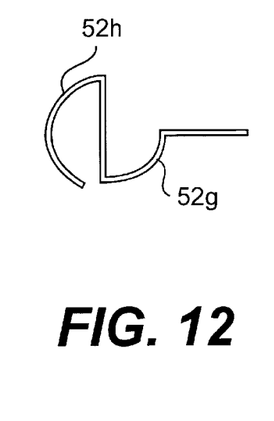
FIG. 12 is a view similar to FIG. 10 showing a third alternative embodiment of a bent reinforcement tube.

As shown in FIGS. 8 and 9, the reinforcement tube 20 is preferably bent in a generally S-shaped configuration with each bend 52a, 52b being a generally rounded bend of approximately 90 degrees. Numerous other bending configurations are also possible. For example, FIG. 10 shows a reinforcement tube with bends 52c, 52d extending approximately 45 degrees, and FIG. 11 shows bends 52e, 52f extending approximately 180 degrees. FIG. 12 shows another alternate embodiment having 90 degree bends 52g, 52h having less rounding than the S-shape of FIG. 9. Although many different types of bends are possible, each bend preferably ranges from approximately 45 degrees to approximately 180 degrees, and more preferably from approximately 85 degrees to approximately 95 degrees.

Other embodiments of the invention will be apparent to those skilled in the art from consideration of the specification and practice of the invention disclosed herein. It is intended that the specification and embodiments described herein be considered as exemplary only.

What is claimed is:

1. A handle assembly for a surgical instrument having a flexible conduit and at least one control member axially movable with respect to the flexible conduit, the handle assembly comprising:
   a body member configured to be coupled to the flexible conduit;
   an actuator movable with respect to the body member, the actuator including at least one projection member; and
   a reinforcement tube having an interior passage sized to accommodate said at least one control member, the reinforcement tube including at least one bend configured to engage the reinforcement tube with the at least one projection member such that movement of the actuator with respect to the body member causes movement of the reinforcement tube,
   wherein the reinforcement tube is curved along said at least one bend.

2. The handle assembly of claim 1, wherein an interior of the reinforcement tube has a reduced cross-section in the region of the at least one bend, the reduced cross-section being configured to retain said at least one control member.

3. The handle assembly of claim 1, wherein the body member includes portions configured to be connected together to retain the flexible conduit therebetween.

4. The handle assembly of claim 3, wherein the portions are connected together via clips on the portions.

5. The handle assembly of claim 3, wherein at least one of the portions of the body member includes ribs configured to engage an outer surface of the flexible conduit.

6. The handle assembly of claim 3, wherein each of the portions has a generally U-shaped cross-section.

7. The handle assembly of claim 1, wherein the body member includes a slot and wherein a portion of the actuator is configured to move in the slot.

8. The handle assembly of claim 1, wherein the actuator includes first and second portions configured to be connected together.

9. The handle assembly of claim 8, wherein the first and second portions of the actuator are connected together via clips on the actuator portions.

10. The handle assembly of claim 8, wherein each of the portions of the actuator includes a projection member configured to engage said at least one bend.

11. The handle assembly of claim 1, wherein the reinforcement tube includes a plurality of bends configured to engage a plurality of projection members on the actuator.

12. A surgical instrument comprising:
the handle assembly of claim 1;
a flexible conduit coupled to the body member; and
at least one control member axially movable in the flexible conduit, a proximal end portion of the control member passing through the reinforcement tube and being coupled to the reinforcement tube.

13. The surgical instrument of claim 12, further comprising:
at least one end effector at a distal end of the flexible conduit, the end effector being linked to the control member such that axial movement of the control member causes activation of the end effector.

14. The surgical instrument of claim 13, wherein the surgical instrument is configured as an endoscopic biopsy instrument and wherein the at least one end effector includes a pair of jaws configured to move toward and away from one another in response to axial movement of the control member.

15. The handle assembly of claim 1, wherein the body member includes a thumb ring and the actuator is configured in the form of a spool.

16. The handle assembly of claim 1, wherein the at least one projection member comprises a plurality of projection members, the reinforcement tube being wrapped at least partially around each of the projection members.

17. The handle assembly of claim 1, wherein said at least one bend is generally S-shaped.

18. The handle assembly of claim 1, wherein said at least one bend ranges from approximately 45 degrees to approximately 180 degrees.

19. The handle assembly of claim 1, wherein the reinforcement tube is wrapped at least partially around a longitudinal axis of the projection member.

20. A handle assembly for a surgical instrument having a flexible conduit and at least one control member axially movable in the flexible conduit, the handle assembly comprising:
a body member including portions configured to be connected together to retain the flexible conduit therebetween; and
an actuator movable with respect to the body member, the actuator being configured to be coupled to the at least one control member such that movement of the actuator with respect to the body member causes movement of the at least one control member,
wherein each of the portions is configured to contact an outer surface of the flexible conduit when the flexible conduit is retained therebetween, and
wherein at least one of the portions of the body member includes ribs configured to engage an outer surface of the flexible conduit.

21. The handle assembly of claim 20, wherein each of the portions has a generally U-shaped cross-section.

22. The handle assembly of claim 20, wherein the actuator includes first and second portions configured to be connected together.

23. The handle assembly of claim 22, wherein the first and second portions of the actuator are connected together via clips.

24. A surgical instrument comprising:
the handle assembly of claim 20;
a flexible conduit coupled to the body member; and
at least one control member axially movable in the flexible conduit, a proximal end portion of the control member being coupled to the actuator.

25. The surgical instrument of claim 24, further comprising:
at least one end effector at a distal end of the flexible conduit, the end effector being linked to the control member such that axial movement of the control member causes activation of the end effector.

26. The surgical instrument of claim 25, wherein the surgical instrument is configured as an endoscopic biopsy instrument and wherein the at least one end effector includes a pair of jaws configured to move toward and away from one another in response to axial movement of the control member.

27. A method of making a handle assembly, the method comprising:
placing at least one control member in a reinforcement tube;
bending the reinforcement tube to form at least one bend in the reinforcement tube, the at least one bend reducing the interior cross-section of the tube and thereby retaining the control member in the reinforcement tube, wherein the reinforcement tube is curved along the at least one bend; and
engaging the reinforcement tube comprising the at least one bend with at least one projection member associated with an actuator movable with respect to a body member such that movement of the actuator with respect to the body member causes movement of both the reinforcement tube and the control member.

28. The method of claim 27, further comprising tensioning the control member during the bending.

29. The method of claim 27, wherein the engaging causes the bend to become wrapped at least partially around the projection member.

30. A handle assembly for a surgical instrument having a flexible conduit and at least one control member axially movable in the flexible conduit, the handle assembly comprising:
a body member including portions configured to be connected together to retain the flexible conduit therebetween; and
an actuator movable with respect to the body member, the actuator being configured to be coupled to the at least one control member such that movement of the actuator with respect to the body member causes movement of the at least one control member,
wherein each of the portions is configured to contact an outer surface of the flexible conduit when the flexible conduit is retained therebetween, and
wherein the body member includes a thumb ring and the actuator is configured in the form of a spool.

31. A method of connecting a handle assembly to a flexible conduit of a surgical instrument, the method comprising:
providing a handle assembly including a body member and an actuator movable with respect to the body member, wherein the body member includes portions configured to be connected together to retain the flexible conduit therebetween;
placing the flexible conduit between the portions of the body member; and
connecting the portions of the body member together to retain the flexible conduit therebetween,
wherein each of the portions contacts an outer surface of the flexible conduit, and
wherein the connecting comprises snap connecting the portions of the body members together while the conduit is therebetween.

32. A handle assembly for a surgical instrument having a flexible conduit and at least one control member axially movable in the flexible conduit, the handle assembly comprising:
- a body member including portions configured to be connected together to retain the flexible conduit therebetween; and
- an actuator movable with respect to the body member, the actuator being configured to be coupled to the at least one control member such that movement of the actuator with respect to the body member causes movement of the at least one control member,
- wherein each of the portions is configured to contact an outer surface of the flexible conduit when the flexible conduit is retained therebetween, and
- wherein the portions are connected together via clips.

33. A handle assembly for a surgical instrument having a flexible conduit and at least one control member axially movable in the flexible conduit, the handle assembly comprising:
- a body member including portions configured to be connected together to retain the flexible conduit therebetween;
- an actuator movable with respect to the body member, the actuator being configured to be coupled to the at least one control member such that movement of the actuator with respect to the body member causes movement of the at least one control member; and
- a reinforcement tube, wherein the actuator comprises at least one projection member and wherein the reinforcement tube includes a plurality of bends configured to engage the reinforcement tube with the projection member,
- wherein each of the portions is configured to contact an outer surface of the flexible conduit when the flexible conduit is retained therebetween.

34. A handle assembly for a surgical instrument having a flexible conduit and at least one control member axially movable with respect to the flexible conduit, the handle assembly comprising:
- a body member configured to be coupled to the flexible conduit;
- an actuator movable with respect to the body member, the actuator including at least one projection member; and
- a reinforcement tube having an interior passage sized to accommodate said at least one control member, the reinforcement tube including at least one bend configured to engage the reinforcement tube with the at least one projection member such that movement of the actuator with respect to the body member causes movement of the reinforcement tube,
- wherein the reinforcement tube is wrapped at least partially around a longitudinal axis of the projection member.

* * * * *